US00PP28617P3

(12) United States Plant Patent
de Bont

(10) Patent No.: US PP28,617 P3
(45) Date of Patent: Nov. 7, 2017

(54) ***ECHINACEA* PLANT NAMED 'HILMOOOJOY'**

(50) Latin Name: *Echinacea purpurea*
Varietal Denomination: HILMOOOJOY

(71) Applicant: Diony de Bont, De Kwakel (NL)

(72) Inventor: Diony de Bont, De Kwakel (NL)

(73) Assignee: Takii Europe B.V., De Kwakel (NL)

( * ) Notice: Subject to any disclaimer, the term of this patent is extended or adjusted under 35 U.S.C. 154(b) by 50 days.

(21) Appl. No.: 14/756,662

(22) Filed: Sep. 29, 2015

(65) Prior Publication Data

US 2017/0094882 P1 Mar. 30, 2017

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

PUBLICATIONS

De Boomkwekerij 2014 Plantarium shows more than 110 new varieties, retrieved on Jan. 18, 2007, retrieved from the Internet at <https://issuu.com/hortipoint/docs/bkw_17a-2014vv> pp. 11 and 20.*

* cited by examiner

*Primary Examiner* — June Hwu
(74) *Attorney, Agent, or Firm* — C. A. Whealy

(57) ABSTRACT

A new and distinct cultivar of *Echinacea* plant named 'Hilmooojoy', characterized by its upright plant habit; moderately vigorous growth habit; strong and healthy roots; dark green-colored leaves; strong flowering stems; numerous large inflorescences with orange-colored ray florets; and good garden performance.

1 Drawing Sheet

Botanical designation: *Echinacea purpurea.*
Cultivar denomination: 'HILMOOOJOY'.

BACKGROUND OF THE INVENTION

The present invention relates to a new and distinct cultivar of *Echinacea* plant, botanically known as *Echinacea purpurea*, and hereinafter referred to by the name 'Hilmooojoy'.

The new *Echinacea* plant is a product of a planned breeding program conducted by the Inventor in De Kwakel, The Netherlands. The objective of the breeding program is to develop new strong and freely flowering *Echinacea* plants with attractive ray and disc floret coloration.

The new *Echinacea* plant originated from an open-pollination in June, 2009 in De Kwakel, The Netherlands of a proprietary selection of *Echinacea purpurea* identified as code designation T 12058 A, not patented, as the female, or seed, parent with an unknown selection of *Echinacea purpurea* as the male, or pollen, parent. The new *Echinacea* plant was discovered and selected by the Inventor as a single flowering plant from within the progeny of the stated open-pollination grown in a controlled greenhouse environment in De Kwakel, The Netherlands in July, 2010.

Asexual reproduction of the new *Echinacea* plant by in vitro meristem culture in a controlled environment in De Kwakel, The Netherlands since September, 2010 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilmooojoy'. These characteristics in combination distinguish 'Hilmooojoy' as a new and distinct *Echinacea* plant:

1. Upright plant habit.
2. Moderately vigorous growth habit.
3. Strong and healthy roots.
4. Dark green-colored leaves.
5. Strong flowering stems.
6. Numerous large inflorescences with orange-colored ray florets.
7. Good garden performance.

Plants of the new *Echinacea* can be compared to plants of the female parent selection. Plants of the new *Echinacea* differ from plants of the female parent selection in the following characteristics:

1. Plants of the new *Echinacea* are more compact than plants of the female parent selection.
2. Plants of the new *Echinacea* have darker green-colored leaves than plants of the female parent selection.
3. Plants of the new *Echinacea* have smaller inflorescences than plants of the female parent selection.
4. Ray florets of plants of the new *Echinacea* are lighter orange in color than ray florets of plants of the female parent selection.

Plants of the new *Echinacea* can be compared to plants of *Echinacea hybrida* 'Orange273', disclosed in U.S. Plant patent application Ser. No. 14/756,660. In side-by-side comparisons conducted in De Kwakel, The Netherlands, plants of the new *Echinacea* differed primarily from plants of 'Orange273' in the following characteristics:

1. Plants of the new *Echinacea* were taller than plants of 'Orange273'.
2. Plants of the new *Echinacea* were more uniform than plants of 'Orange273'.
3. Plants of the new *Echinacea* had smaller inflorescences than plants of 'Orange273'.
4. Ray florets of plants of the new *Echinacea* were lighter orange in color than ray florets of plants of 'Orange273'.

BRIEF DESCRIPTION OF THE PHOTOGRAPH

The accompanying photograph illustrates the overall appearance of the new *Echinacea* plant showing the colors as true as it is reasonably possible to obtain in colored reproductions of this type. Colors in the photograph may differ slightly from the color values cited in the detailed botanical description which accurately describe the colors of the new *Echinacea* plant.

The photograph is a side perspective view of a typical flowering plant of 'Hilmooojoy' grown in a container.

DETAILED BOTANICAL DESCRIPTION

The aforementioned photograph and following observations and measurements describe plants grown during the spring and early summer in 17-cm containers in a glass-covered greenhouse and "finished" in an outdoor nursery in De Kwakel, The Netherlands under cultural practices typically used in commercial *Echinacea* production. During the production of the plants, day temperatures ranged from 12° C. to 20° C. and night temperatures ranged from 7° C. to 15° C. Plants used for the photograph and description were 20 weeks old. In the following description, color references are made to The Royal Horticultural Society Colour Chart, 2007 Edition, except where general terms of ordinary dictionary significance are used.

Botanical classification: *Echinacea purpurea* 'Hilmooojoy'.

Parentage:

*Female parent*.—Proprietary selection of *Echinacea purpurea* identified as code designation T 12058 A, not patented.

*Male parent*.—Unknown selection of *Echinacea purpurea*, not patented.

Propagation:

*Type*.—By in vitro meristem culture.

*Time to initiate roots, summer*.—About five weeks at temperatures about 20° C. for the first two weeks, then at temperatures about 12° C. to 14° C.

*Time to initiate roots, winter*.—About six weeks at temperatures about 20° C. for the first two weeks, then at temperatures about 14° C. to 20° C.

*Time to produce a rooted young plant, summer*.—About five weeks at temperatures about 14° C. to 20° C.

*Time to produce a rooted young plant, winter*.—About six weeks at temperatures about 18° C.

*Root description*.—Medium in thickness, fibrous; strong and healthy; typically white to brown in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Herbaceous perennial; upright plant habit, narrow inverted triangle; freely branching habit with about 21 branches developing per plant; moderately vigorous growth habit.

*Plant height*.—About 54.4 cm.

*Plant diameter or spread*.—About 35.2 cm.

*Lateral branches*.—Length: About 31.9 cm. Diameter: About 6 mm. Internode length: About 3.3 cm. Aspect: Erect to about 20° from vertical. Strength: Strong. Texture: Sparsely to moderately pubescent, strigose; rough. Color: Close to 144A to 144B.

Leaf description:

*Basal leaves*.—

*Arrangement*.—Alternate, simple.

*Length*.—About 10.1 cm.

*Width*.—About 2.7 cm.

*Shape*.—Narrowly ovate.

*Apex*.—Narrowly acute.

*Base*.—Attenuate.

*Margin*.—Entire; moderately undulate.

*Texture, upper and lower surfaces*.—Moderately pubescent, strigose; rough.

*Luster, upper and lower surfaces*.—Matte.

*Venation pattern*.—Pinnate.

*Color*.—Developing leaves, upper surface: Slightly darker than 143A. Developing leaves, lower surface: Close to 143A. Fully expanded leaves, upper surface: Close to N137B; venation, close to 147C. Fully expanded leaves, lower surface: Close to 147B; venation, close to 138C.

*Petioles, basal leaves*.—Length: About 4.2 cm. Diameter: About 2.5 mm by 3 mm. Strength: Strong, flexible. Texture, upper surface: Smooth, glabrous. Texture, lower surface: Sparsely pubescent, strigose. Color, upper surface: Close to 144C; margins, close to N137B. Color, lower surface: Close to 144B; margins, close to 137B.

*Cauline leaves*.—

*Arrangement*.—Alternate, simple.

*Length*.—About 5.5 cm.

*Width*.—About 1.8 cm.

*Shape*.—Narrowly ovate.

*Apex*.—Narrowly acute.

*Base*.—Attenuate.

*Margin*.—Entire.

*Texture, upper and lower surfaces*.—Moderately pubescent, strigose; rough.

*Luster, upper and lower surfaces*.—Matte.

*Venation pattern*.—Pinnate.

*Color*.—Developing leaves, upper surface: Slightly darker than 143A. Developing leaves, lower surface: Close to 143A. Fully expanded leaves, upper surface: Close to N137B; venation, close to 147C. Fully expanded leaves, lower surface: Close to 147B; venation, close to 138C.

*Petioles, cauline leaves*.—Length: About 6 mm. Diameter: About 2 mm by 2 mm. Strength: Strong, flexible. Texture, upper and lower surfaces: Pubescent, rough. Luster, upper and lower surfaces: Matte. Color, upper surface: Close to N137B. Color, lower surface: Close to 147B.

Inflorescence description:

*Appearance*.—Terminal rotate single-type inflorescences with ray and disc florets arranged on a capitulum; inflorescences positioned upright above the foliar plane on mostly upright and strong peduncles.

*Flowering habit*.—Freely flowering habit with about 21 inflorescences per plant at one time.

*Fragrance*.—Faint; sweet, pleasant.

*Time to flower*.—Plants begin flowering about 13 to 18 weeks after planting; in the garden, plants flower continuously from mid-June to late September in The Netherlands.

*Inflorescence longevity*.—Inflorescences maintain good substance for about three weeks on the plant; inflorescences persistent.

*Inflorescence buds*.—Height: About 2 cm. Diameter: About 2.8 cm. Shape: Flattened globular. Color: Involucral bracts, close to 143A and 138B; ray florets, close to 29B to 29C, towards the apex, close to 150B.

*Inflorescence size*.—Diameter: About 8.8 cm. Depth (height): About 3.1 cm. Disc diameter: About 3 cm. Receptacle height: About 1.2 cm. Receptacle diameter: About 1 cm. Receptacle color: Close to N155A.

*Ray florets*.—Quantity and arrangement: About 19 arranged in a single whorl at the base of the receptacle. Length: About 4.1 cm. Width: About 7 mm. Shape: Oblanceolate. Apex: Praemorse to deeply emarginate. Base: Cuneate. Margin: Entire. Texture, upper surface: Smooth, glabrous; moderately velvety. Texture, lower surface: Smooth, glabrous. Luster, upper and lower surfaces: Matte. Aspect: Horizontal to drooping, about 20° from horizontal. Color: When opening, upper surface: Close to N25B. When opening, lower surface: Close to 29B; margins, close to 34B. Fully opened, upper surface: Close to 34C; towards the base, close to N34A; main color becoming closer to 31A to 31B with development. Fully opened, lower surface: Close to 31C; margins, close to N34C; color becoming closer to N34C with development.

*Disc florets*.—Length: About 6 mm. Diameter: About 2.5 mm. Shape: Tubular, apices acute. Number of disc florets per inflorescence: About 250. Texture, inner and outer surfaces: Smooth, glabrous. Luster, inner and outer surfaces: Glossy. Color, immature, inner and outer surfaces: Apex: Close to 143A. Mid-section and base: Close to 145B. Color, mature, inner and outer surfaces: Apex: Close to 146A tinged with close to 178B. Mid-section and base: Close to 143A to 143B.

*Receptacle spines*.—Quantity: One per disc floret. Shape: Acicular. Apex: Narrowly acute. Base: Attenuate. Texture: Smooth, glabrous. Luster: Glossy. Color: Apex: Close to between 53A and 203A. Mid-section: Close to 143A. Base: Close to 144B.

*Involucral bracts*.—Quantity per inflorescence: About 48 arranged in about four whorls. Length: About 1 cm. Width: About 3 mm. Shape: Ovate. Apex: Acute. Base: Cuneate. Margin: Entire. Texture, upper surface: Smooth, glabrous. Texture, lower surface: Mostly glabrous; margins, sparsely to moderately pubescent. Color, upper surface: Close to 143A to 143B. Color, lower surface: Close to 143B.

*Peduncles*.—Length: About 12.6 cm. Diameter: About 4.5 mm. Strength: Strong. Aspect: Upright. Texture: Sparsely pubescent, strigose. Color: Close to 144A.

*Reproductive organs*.—Androecium (present on ray and disc florets): Quantity per floret: About five. Filament length: About 5 mm. Filament color: Close to 145D. Anther shape: Narrowly oblong. Anther length: About 2.5 mm. Anther color: Close to 200A to 200B. Pollen amount: Scarce. Pollen color: Close to 17A. Gynoecium (present only on disc florets): Quantity per floret: One. Pistil length: About 7 mm. Stigma shape: Decurrent, unequal. Stigma color: Close to 183A. Style length: About 6 mm. Style color: Close to 145B. Ovary color: Close to 145D. Seeds and fruits: Seed and fruit development have not been observed on plants of the new *Echinacea*.

Disease & pest resistance: Plants of the new *Echinacea* have not been shown to be resistant to pathogens and pests common to *Echinacea*.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Hilmoooo-joy' as illustrated and described.

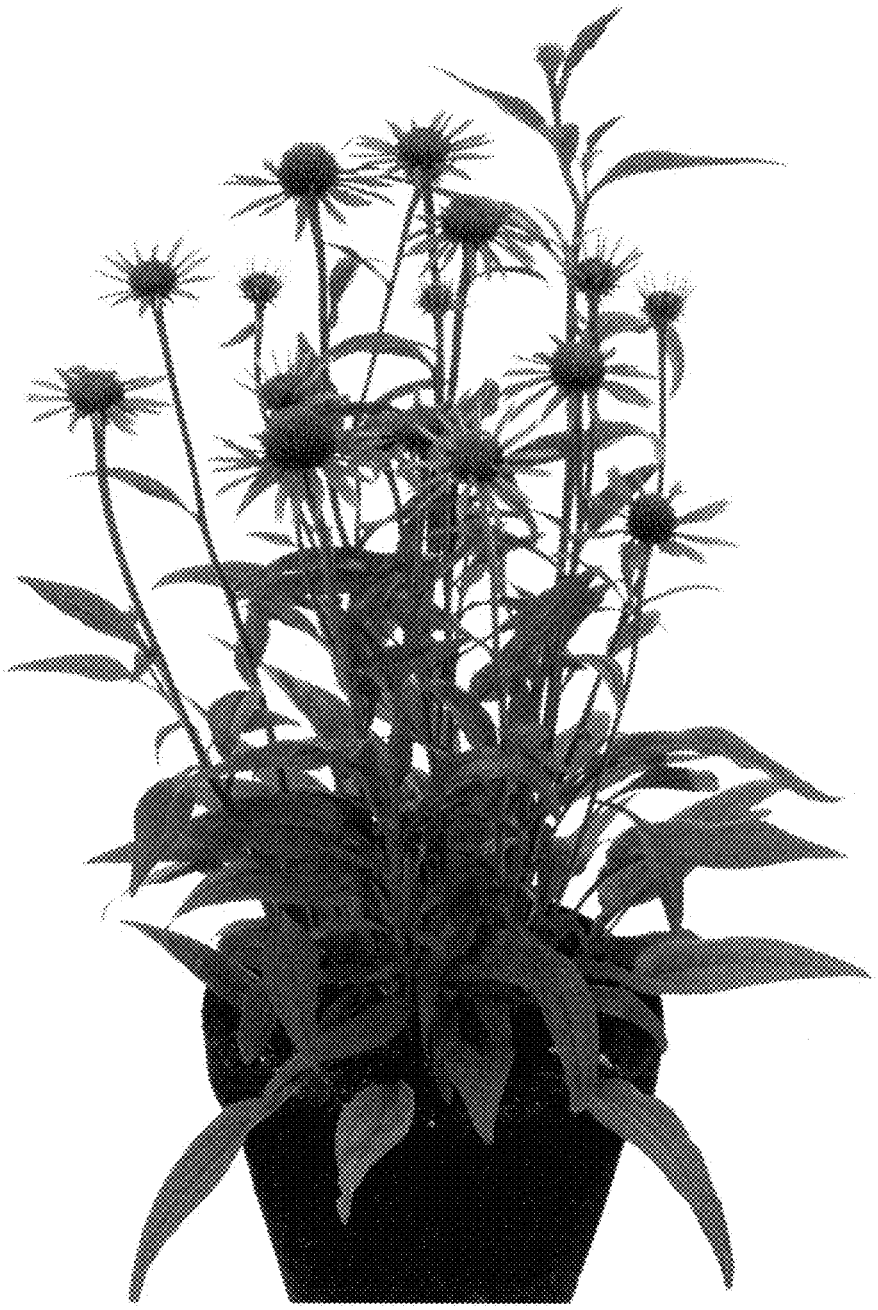

* * * * *